(12) United States Patent
Tanhehco

(10) Patent No.: US 6,797,857 B2
(45) Date of Patent: Sep. 28, 2004

(54) SOLIDIFIER FOR A LIQUID

(75) Inventor: Benito L. Tanhehco, Powell, TN (US)

(73) Assignee: DeRoyal Industries, Knoxville, TN (US)

(*) Notice: Subject to any disclaimer, the term of this patent is extended or adjusted under 35 U.S.C. 154(b) by 208 days.

(21) Appl. No.: 09/865,141

(22) Filed: May 24, 2001

(65) Prior Publication Data

US 2002/0185156 A1 Dec. 12, 2002

(51) Int. Cl.$^7$ .............................................. A61F 13/15
(52) U.S. Cl. .................. 604/368; 604/319; 604/323; 604/333; 134/6; 134/7; 134/8; 134/21; 134/22.1; 134/116; 424/405
(58) Field of Search .......................... 134/6, 7, 8, 21, 134/22.1, 116, 116 R; 604/319, 323, 333, 368; 424/405

(56) References Cited

U.S. PATENT DOCUMENTS

| 4,748,069 A | 5/1988 | Cullen |
| 4,749,600 A | 6/1988 | Cullen et al. |
| 4,853,266 A | 8/1989 | Cullen |
| 5,356,678 A | 10/1994 | Heitzhaus et al. |
| 6,380,130 B1 * | 4/2002 | Meyer et al. ............... 502/401 |

* cited by examiner

Primary Examiner—Randy Gulakowski
Assistant Examiner—Gentle E Winter
(74) Attorney, Agent, or Firm—Pitts & Brittian, PC

(57) ABSTRACT

A solidifier for a liquid, the solidifier comprising a mixture of absorbents having different apparent densities whereby at least one absorbent is negatively buoyant and at least one absorbent is positively buoyant relative to the liquid sought to be solidified. Packaging for the solidifier is disclosed for effecting selective dispersal of the solidifier within the liquid sought to be solidified.

13 Claims, 1 Drawing Sheet

SOLIDIFIER FOR A LIQUID

BACKGROUND OF INVENTION

This invention relates to chemical compounds which are useful in converting liquids to a non-pourable state, for example. The invention is particularly useful in medical applications for converting waste (infectious) medical liquids or semi-liquids to a substantially non-pourable state for ready handling and disposal.

In the field of liquid waste handling, there are known several powdered super-absorbent compounds (at times referred to herein as "absorbents") which can solidify, or convert to a gel, a large volume of liquid relative to the volume or weight of the absorbent introduced into the liquid. One major use of such absorbents is to convert a volume of liquid to a solid, semi-solid (e.g., a gel) form to make the liquid sufficiently stable for recovery of spilled liquid or to convert the liquid into a form which is reasonably stable for clean-up (spills), handling (shipping/transfer), storage and/or disposal. With many liquid wastes, employee safety and/or environmental concerns dictate quick action to minimize the distribution of a spilled flowable waste, hence the need for rapid solidification of the liquid. In certain medical situations, time is of the essence and avoidance of inadvertent spillage of liquid waste is most important, hence another example where rapid solidification of such liquid waste is important, or even critical.

"Solidification" or "stabilization", as these terms are used herein is intended to refer to the alteration of the state of a flowable material (usually a liquid) to a substantially non-flowable material. The "flowable" material may be a liquid or in a gel or semi-solid state, so that if the material were contained within an open-top vessel, the material would readily "flow" from the vessel when the vessel was tilted, for example. A "non-flowable" material may be a solid or substantially a solid (as in a gel) such that the material would not readily flow from a tilted vessel containing the material. "Solidifier", as used herein, is intended to include two or more absorbents. The solidifier may comprise a single mixture of the absorbents, or in other instances, may comprise two or more absorbents (or mixtures of absorbents).

In the prior art super-absorbents have been employed in many applications, such as in oil spills where the super-absorbent, applied in liquid or powder form stems the distribution of the spill and renders the oil more readily retrieved or collected. In medial applications, super-absorbents have been used heretofore for stabilizing liquid infectious waste within a container against spillage through inadvertent tipping of the container in the course of a medical procedure, or during transfer, storage and/or disposal of the waste.

Super absorbents may be characterized by a variety of properties. In the present invention, one such property is the apparent density (also termed "bulk density") of the super absorbent relative to other super absorbents and/or relative to the density of the liquid sought to be stabilized. For example, the super absorbent may either sink or float with respect to the liquid sought to be stabilized. For example, in the instance of an oil spill, the immediate concern commonly is to deter seepage of the oil into the ground. In this situation, an absorbent having a density greater than the oil would be desired so that the absorbent would "sink" relative to the oil and solidification of the oil would commence at the bottom of the layer of spilled oil. On the other hand, it might be desirable when dealing with a container of liquid waste, that the solidification commence adjacent the surface of the liquid to quickly form a "solid cap" on the surface of the liquid whereby spillage or splashing of the liquid from the container is minimized while the remainder of the liquid in the container is being stabilized.

It has been found by the present inventor that in certain instances, the apparent density of the absorbent, relative to the density of the liquid sought to be stabilized, can present problems, in that a relatively lower density absorbent may quickly form a cap on the surface of a liquid and preclude the migration of absorbent to other portions of the liquid. Vice versa, if the absorbent is more dense than the liquid, the absorbent quickly sinks to the bottom of a container of liquid and commences solidification of that liquid adjacent the bottom of the container and traps absorbent within the solidified liquid so that there is little, slow or no solidification of the remaining liquid within the container. The mixture(s) may be packaged for controlled release into a liquid sought to stabilized.

It is an object of the present invention to provide a novel solidifier for flowable materials, such as liquids.

It is another object of the present invention to provide a method for the controlled stabilization of a flowable material throughout the overall volume of the flowable material.

SUMMARY OF INVENTION

Figures 1, 2:
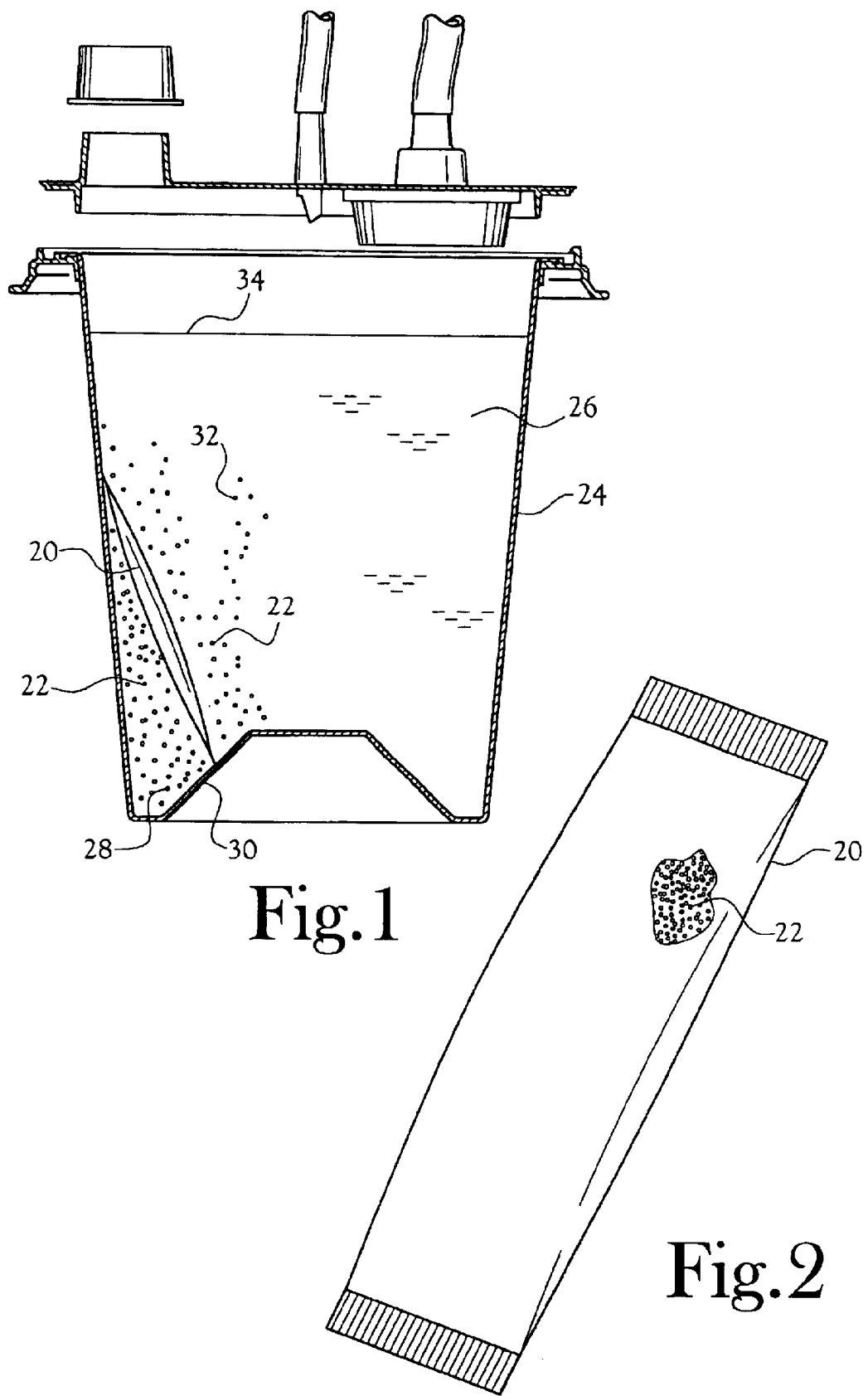
FIG. 1 is a schematic diagram of a package containing a mixture of absorbents in accordance with one aspect of the present invention.
FIG. 2 is a schematic representation of a package containing a mixture of absorbents disposed in a liquid to be solidified.

In accordance with one aspect of the present invention, the present inventor has discovered a solidifier which comprises a plurality of components, particularly including absorbents having preselected properties, particularly apparent (bulk) densities, which in combination provide unique stabilization results. In the present invention, the "density" of the absorbent takes into consideration the bulk density of the absorbent. These, and/or other "density" factors are used to determine whether the absorbent "floats" or "sinks" when introduced into the liquid sought to be stabilized. For example, whether a given absorbent, or mixture of absorbents, floats or sinks with respect to a liquid may be influenced by factors such as the overall shape of the particles of the absorbent, wetability of the absorbent particle by the liquid, entrapment of air, etc., as well as the specific gravity of the particles of the absorbent. Thus, the terms "floaters" and "sinkers" as used herein at times to characterize a given absorbent or mixture of absorbents, refers to whether the absorbent or mixture of absorbents, as a whole, starts its activation process predominantly adjacent the bottom of the container or adjacent the surface of the liquid in the vessel.

In one solidifier, there is provided a mixture of a first absorbent having an apparent bulk density and buoyancy which is negative relative to the liquid sought to be stabilized and a second absorbent having an apparent density and buoyancy which is positive relative to the liquid sought to be stabilized. Depending upon the desired progression of solidification and/or the rate of solidification sought, the mixture of absorbents may be selected to provide a very large variety of solidification effects within a given liquid, and particularly within a container of the liquid.

In accordance with another aspect of the present invention, the present inventor provides controlled dispersion of two or more absorbents within a liquid, in one instance by selection of the apparent densities and buoyancy of the absorbents relative to the density of the liquid sought to be stabilized, and in another instance through selection of the dispersion of the absorbents by means of the packaging employed.

DETAILED DESCRIPTION OF INVENTION

There is a variety of manufacturers of super-absorbents in the marketplace. Generally, super-absorbents comprise a polymer such as sodium polyacrylate(s). Also generally, a super-absorbent is available in a powder form and will either be negatively buoyant or positively buoyant in a 0.9% saline solution, for example, depending upon the apparent (bulk) density of the absorbent. Typically an apparent density of the absorbent below about 0.5 g/cm$^3$ will result in a positive buoyancy, while an apparent density of the absorbent of about 0.7 g/cm$^3$ will result in a negative buoyancy in a 0.9% saline solution.

For present purposes, examples of the present invention are presented with respect to medical liquid wastes as typified by a 0.9% saline solution at room temperature. Given the parameters set forth herein, one skilled in the art may readily compound other like effective solidifiers for other liquids. In all instances, however, it is critical to the present invention that there be a predetermined relationship between the buoyancy of each absorbent employed relative to the liquid sought to be stabilized.

With respect to liquid medical waste applications, several specific absorbent compounds, all available in powder form, have been identified to achieve the desired buoyancy characteristics of the present solidifier. For example, in the positive buoyancy category Absorb-O-Gel™, available from Pioneer Medical, Aqua-Keep™ J550, manufactured by Sumitomo and available from Absorbent Technologies and Norscoryl™ S-35, manufactured by Emerging Technologies, Inc. and available through The Chemical Company, all have bulk densities that result in positive buoyancy relative to the referent saline solution. Also, in the negative buoyancy category Medigel™ 300, available from BASF, Flosorb™ 60, available from Chemtall, Inc., and SA60N type II, available from Absorbent Technologies, all have a bulk density which results in a negative buoyancy relative to the referent saline solution. Stated generally, floater absorbents absorb faster (hence solidify faster) that do sinkers, but have a lower absorbing capacity relative to sinkers. Also, the rate of solidification is dependent upon the ratio of the amount of the absorbent uses per given volume of liquid. Still further, the speed and capacity of solidification of a given absorbent varies according to the type of solution being treated. For example, the solidification action of sodium-based polyacrylate absorbent in a saline solution is of lesser capacity than the solidification action of this absorbent in tap water, for example.

In accordance with one aspect of the present invention, a combination of floating and sinking powdered absorbents is provided. In one embodiment, the specific mixture includes between about 20% and 80%, by weight, of a sinking absorbent and between about 20% and 80%, by weight, of the floating absorbent. A mixture of absorbents within these stated ranges of weight percentages, provides for relatively uniform (over time) conversion of the referent liquid to a gel. Greater percentages of the sinking absorbent promotes earlier commencement of solidification of the liquid adjacent the bottom of the container of liquid, relative to the commencement and completion of solidification of the liquid adjacent the surface of the liquid in the container. In similar manner, lesser percentages of the sinking absorbent reverses this commencement of solidification of the liquid within the container.

In the foregoing example of percentages of absorbents, the mixture of powdered absorbents is presumed to be introduced into the container of liquid in the form of a flowing stream of substantially uniform volume of the mixture, and that the two absorbents commence and complete their solidification effect at substantially the same rate of solidification. In those instances where it is desired that the solidification of the liquid commence and attain completion adjacent the bottom of the container, in addition to the relative bulk densities of the two absorbents, one need take into consideration the relative rates at which the two absorbents effect solidification. Faster-acting absorbents, either a floater or a sinker, can create undesirable, or even deleterious effects. For example, even when the mixture is of substantially equal quantities, by weight, of the two absorbents, if the floater absorbent is faster-acting than the sinker absorbent, the faster-acting absorbent may form a solid or semi-solid cap at the surface of the liquid which captures or precludes the movement of the sinker absorbent past the cap, thereby resulting in incomplete solidification of the remainder of the liquid within the container. On the other hand, if the sinker absorbent of this mixture is the faster-acting absorbent, then the solidification of the liquid may proceed "from the bottom up" within the container, which can be a desired result, but would not be desired where a minimum time for full solidification of the liquid was a critical desired result.

In any event, the present combination of absorbents provides a benefit over the use of a single absorbent. More specifically, when using a single absorbent, solidification can only commence and proceed to completion either from the top-down or from the bottom-up within the container. In either of these situations, the cap which is initially formed tends to capture a portion of the absorbent within the cap and delay the migration of the absorbent to other portions of the liquid. Where time is of the essence, such action is not acceptable, as in medical waste liquids. Morever, where time is not of the essence, single absorbents tend to incompletely disperse throughout the liquid, leaving pockets of liquid within the container—a situation which can be disastrous when handling medical waste.

In the mixture of the present invention, while the caps may form, the fact that the absorbent works from both the bottom-up and from the top-down, greatly enhances the ability of the absorbent to fully solidify or gel the liquid waste and do so in a timely fashion. This combination also eliminates the need for stirring of the liquid to ensure distribution of the absorbent within the liquid, which action can splash liquid from the container or other spillage from the container.

The following examples set forth two tests record the times consumed in solidification of 500 cc of tap water at room temperature employing different percentages compositions of sinkers and floaters, and provide guidance to one skilled in the art for formulating further mixtures, etc.:

Fifteen grams of a powder mixture of Flosorb™ 60 sinker, having an apparent density of about 0.7 and Aqua Keep™ J550, having an apparent density of about 0.4, employing the percentages by weight given in the following Tables was added via a funnel to a vessel containing 500 cc of tap water. The powder mixture was poured through the funnel at a uniform rate of 7 gm/sec, without stirring. No substantial clumping of the mixture within the liquid was noted. The predominant portion of the particles of the Flosorb™ 60 was in the range of 500 to 800 micrometers, and in the range of 100–200 micrometers for the AquaKeep J550. The observed times for solidification of the water in the container are given in the Table I.

TABLE I

| Sinker (% by wt.) | Floater (% by wt.) | Time to Solidify (sec) |
|---|---|---|
| 100 | 0 | 150 |
| 80 | 20 | 90 |
| 60 | 40 | 30 |
| 40 | 60 | 28 |
| 20 | 80 | 38 |
| 0 | 100 | 40 |

A further test was conducted identically with the test described hereinabove except the sinker was BASF 2102 and the floater was Norscoryl S35 (predominant particle size range of 100–500 micrometers.

TABLE II

| Sinker (% by wt.) | Floater (% by wt.) | Time to Solidify (sec) |
|---|---|---|
| 100 | 0 | 240 |
| 80 | 20 | 74 |
| 60 | 40 | 60 |
| 40 | 60 | 45 |
| 20 | 80 | 40 |
| 0 | 100 | 37 |

In a further test, the sinker of the second test, at 100% by wt., clumped significantly when added to the water, but when mixed with the floater, no significant clumping of the mixture was noted. Avoiding clumping of the mixture within the liquid is of major import in the present invention, even more significant than the formation of caps at the top or bottom of the liquid, in that clumping prohibits full utilization of the quantity of the mixture and less than complete solidification per unit of absorbent used.

In similar manner, the present inventor has discovered that inclusion in a mixture of a sinker absorbent and a floater absorbent, a third absorbent which also is a sinker, and which may have the same bulk density but a particle shape different from the other sinker absorbent, one can achieve more complete and uniform dispersion of the more dense sinker. This effect has been found also to be enhanced by choosing a third sinker absorbent which has a larger average particle size than does the more dense sinker. In one test, 50% by weight of Aqua-Keep J550 (floater) was mixed with 10% by weight of ASAP 2102 ("light sinker") and 40% by weight of Flosorb 60 ("heavy sinker"). This mixture exhibited enhanced dispersion of the Flosorb 60 absorbent as compared to the dispersion of the Flosorb 60 employed without the second sinker absorbent.

In a further embodiment of the present invention, a second sinker absorbent was added to the two-absorbent mixture to produce a three-component mixture of absorbents. This added sinker was found to enhance the dispersion of all of the absorbents throughout the volume of the liquid, particularly the dispersion of the sinkers. In one example, 50% by wt. of Flosorb™ 60 (first sinker), 10% by wt. of BASF 2102 (second sinker) and 40% by wt. of Absorb-O-Gel (floater) were mixed to define a three component absorbent system. This mixture exhibited the described enhancement of dispersion of the several absorbents of the mixture, particularly the dispersion of the sinkers. Having this knowledge, one skilled in the art will recognize that through the choice of the three components of the mixture, one can obtain substantially simultaneous solidification at the bottom, top and central portions of the liquid, hence enhanced reduction of solidification time.

It will be recognized by one skilled in the art that the relative percentages of the absorbents used may be varied to suit particular waste concerns. For example, in some types of waste it may be desired for more of the solidification to take place from the bottom-up, but it is still desired to have a buoyant absorbent to form a cap at the top surface of the liquid while solidification takes place. In this instance, the relative percentage of sinker absorbent may be increased and the percentage of floater absorbent may be relatively decreased. Such a situation might occur when there is primary concern about the liquid waste seeping form the bottom, but the floating cap would also be useful minimizing evaporation of the liquid or in minimizing flow of the liquid beyond the immediate area. Conversely, the relative percentages may be adjusted in the opposite manner where flow of the liquid, or spillage from some type of vessel that must be moved, is the primary concern, but seepage from the bottom or simply more rapid solidification, is also a concern.

In accordance with the basic concept of the present invention one can either prevent or use to one's advantage the potential stratification issues that arise due to the use of only a single absorbent which has a given buoyancy relative to the liquid to be solidified. This advantage is accomplished through the use of multiple absorbents mixed together, preferably in powder form, and introduced into the body of liquid to be solidified in a substantially uniform flowing stream of the mixture, such absorbents being chosen on the basis of their buoyancies relative to the liquid to be solidified.

In accordance with another aspect of the present invention, the manner of introduction of the mixture of absorbents into the liquid has been found by the present inventor to be of importance. In this respect, packaging of the powder mixture can be selected to accomplish controlled delivery of selected quantities of a given absorbent, or a given mixture of absorbents, or both, into the liquid to be solidified. FIG. 1 depicts one embodiment of an elongated package containing a mixture of absorbent(s). In one embodiment, the packaging material is of a material which is soluble in the liquid which is to be solidified. For example, a package formed of rice paper or even a light basis weight cellulosic paper may be employed when dealing with liquid medical wastes. This same packaging material may be employed with other liquids also. Specific soluble packaging materials include Acetate Dissolvo and Alcohol Dissolvo fabric from CMS Gilbreth Packaging Systems, Inc.

In the embodiment of FIG. 1, the package 20 was filled with a mixture 22 of 50% by wt. of Aqua-Keep J550, 10%, by wt. of ASAP 2102 and 40% by wt. of Flosorb 60. The packaging material for the depicted package was polyvinyl alcohol which readily absorbs in most liquid medical wastes. As depicted in FIG. 2, upon admission of the package 20 of absorbent mixture into a vessel 24 containing a liquid 26 to be solidified, the package commences dissolving and the contents 22 thereof are released into the liquid. Thereupon, the sinkers 28 tend to gravitate to the bottom 30 of the container and the floaters 32 tends to rise toward the top surface 34 of the liquid, thereby substantially distributing the absorbents to their respective desired locations within the liquid. Through the use of an elongated package, there is a greater likelihood that the package will enter the liquid and lodge within the container with one end of the package disposed adjacent the bottom of the container and the opposite end of the package being disposed above the bottom of the container, thereby enhancing the distribution of the mixture within the liquid in the container and resultant enhanced speed and completeness of solidification of the liquid. Irrespective of the ultimate orientation of a package of a mixture of absorbents, the use of a packaged mixture of absorbents provides greater dispersion of the absorbents, as compared to pouring of the mixture into a container, thereby enhancing the desired stabilization of a liquid in a vessel.

Another packaging related embodiment relates to the segregation of the different buoyant absorbents into different packaging compartments of an overall singular package with the overall packaging made of a material which dissolves or disintegrates when immersed within the liquid to be solidified. In this embodiment, each absorbent is placed with a different compartment in the packaging and each compartment is engineered with different decomposition or dissolving effects. For example, if the combination is of floating and sinking absorbents and the desire is to release the sinker first, so that it does not become trapped by the floater, the packaging would be engineered so that the compartment containing the sinker would dissolve or disintegrate first, thus releasing the sinker first. This type of packaging engineering may utilize a thicker wall-thickness of the dissolving or disintegrating packaging for containing the floater so that this component would be released last, or may utilize different packaging materials of different rates of dissolution or disintegration. One skilled in the art will readily recognize similar packaging concepts as well as a mixture of absorbents in one or both of the different compartments of the package. For example, inner and outer packages, the outer packages containing the first-to-be released absorbent and the inner package containing the second-to-be released absorbent, etc.

Additionally, the buoyancy of the package itself may be engineered to achieve further solidification effects. For example, the complete package may be designed to be negatively buoyant so that the package would sink to the bottom of a vessel containing the liquid to be solidified. There, the package would dissolve, releasing the sinker absorbent and allowing the floater absorbent to rise within the liquid. The converse, that is, designing the package to be positively buoyant, would result in release of both the floated and sinker absorbents, the floater absorbent being adjacent the top surface of the liquid while the sinker sank toward the bottom of the liquid.

Staged release packaging may also be employed, wherein a portion of a mixture of absorbents is released over time, such as in the course of sinking of the overall package toward the bottom of the vessel which contains the liquid.

The foregoing description of various embodiments is provided for purposes of illustration and not limitation. One skilled in the art will recognize numerous changes, additions, substitutions or deletions to the features and components described herein. For example, while specific absorbents have been listed and/or described, a variety of other absorbents may be substituted or included in a mixture of absorbents for a given set of circumstances involving solidification of a liquid or a mixture of liquids, etc., without departing from the scope of the present invention.

What is claimed:

1. A solidifier for the solidification of a volume of liquid having a reference density, said solidifier comprising:

a first absorbent, a second absorbent, a third absorbent, said first absorbent having an apparent density less than the reference density, whereby said first absorbent is positively buoyant relative to the liquid sought to be solidified, said second absorbent having an apparent density greater than the reference density, whereby said second absorbent is negatively buoyant relative to the liquid sought to be solidified, said third absorbent having an apparent density less than the reference density, whereby said third absorbent is positively buoyant relative to the liquid sought to be solidified, said third absorbent apparent density being intermediate the apparent densities of said first and second absorbents, said first, second and third absorbents being combined in a mixture thereof, said mixture comprising about fifty percent, by weight, of said second absorbent, about ten percent, by weight, of said third absorbent, and about forty percent, by weight, of said first absorbent, whereby when said first absorbent, said second absorbent and said third absorbent are introduced into the liquid, said first absorbent, said second absorbent and said third absorbent convert the liquid into a gel.

2. The solidifier of claim 1 wherein the average particle size of said third absorbent is greater than the average particle size of said second absorbent.

3. The solidifier of claim 1 wherein each of said first, second and third absorbents is in the form of a flowable powder.

4. The solidifier of claim 1 and further including packaging for said mixture which is dissolvable or disintegrative when disposed in said liquid to be solidified.

5. A method for the solidification of a liquid having a reference density, said method comprising the steps of:

mixing together a first absorbent, a second absorbent and a third absorbent, said first absorbent having an apparent density less than the reference density, whereby said first absorbent is positively buoyant relative to the liquid to be solidified whereby said first absorbent floats adjacent the surface of the liquid, said second absorbent having an apparent density greater than the reference density whereby said second absorbent is negatively buoyant relative to the liquid to be solidified whereby said second absorbent sinks toward the bottom of the liquid to be solidified, said third absorbent haunt an apparent density intermediate the densities of said first and second absorbents and which renders said third absorbent negatively buoyant relative to the liquid to be solidified, and introducing at least a portion of said mixture into the liquid to be solidified, whereby said first absorbent, and second absorbent and said third absorbent convert the liquid into a gel.

6. The method of claim 5 wherein said third absorbent exhibits an average particle size greater than the average particle size of said second absorbent.

7. A solidifier for the solidification of a volume of liquid having a reference density, said solidifier comprising:

a first absorbent, a second absorbent, a third absorbent, said first absorbent having an apparent density less than the reference density, whereby said first absorbent is positively buoyant relative to the liquid sought to be solidified, said second absorbent having an apparent density greater than the reference density, whereby said second absorbent is negatively buoyant relative to the liquid sought to be solidified, said third absorbent having an apparent density less than the reference density, whereby said third absorbent is positively buoyant relative to the liquid sought to be solidified, said third absorbent apparent density being intermediate the apparent densities of said first and second absorbents, said solidifier comprising about fifty percent, by weight, of said second absorbent, about ten percent, by weight, of said third absorbent, and about forty percent, by weight, of said first absorbent, whereby when said first absorbent and said second absorbent are introduced into the liquid, said first absorbent and said second absorbent convert the liquid into a gel.

8. The solidifier of claim 7 wherein the average particle size of said third absorbent is greater than the average particle size of said second absorbent.

9. The solidifier of claim 7 wherein each of said first absorbent, said second absorbent and said third absorbent is in the form of a flowable powder.

10. The solidifier of claim 7 further comprising packaging for said first absorbent, said second absorbent, and said third absorbent, said packaging being dissolvable or disintegrative when disposed in said liquid to be solidified.

11. The solidifier of claim 10 wherein said packaging comprises two or more compartments, each compartment containing a portion of one or more of said first absorbent, said second absorbent, and said third absorbent.

12. The solidifier of claim 11 wherein said two or more compartments exhibit different rates of dissolution or disintegration when disposed in said liquid to be solidified.

13. A solidifier for the solidification of a volume of liquid having a reference density, said solidifier comprising:

a first absorbent;

a second absorbent;

a third absorbent; and packaging for said first absorbent, said second absorbent, and said third absorbent, said packaging being dissolvable or disintegrative when disposed in said liquid to be solidified, said packaging comprising two or more compartments, each compartment containing a portion of one or more of said first absorbent, said second absorbent, and said third absorbent, said two or more compartments exhibiting different rates of dissolution or disintegration when disposed in said liquid to be solidified;

said first absorbent having an apparent density less than the reference density, whereby said first absorbent is positively buoyant relative to the liquid sought to be solidified;

said second absorbent having an apparent density greater than the reference density, whereby said second absorbent is negatively buoyant relative to the liquid sought to be solidified;

whereby when said first absorbent, said second absorbent and said third absorbent are introduced into the liquid, said first absorbent, said second absorbent and said third absorbent convert the liquid into a gel.

* * * * *